United States Patent
Reich et al.

(10) Patent No.: US 9,913,712 B2
(45) Date of Patent: Mar. 13, 2018

(54) INTRAOCULAR ACCOMMODATING LENS AND METHODS OF USE

(71) Applicant: ForSight Labs, LLC, Menlo Park, CA (US)

(72) Inventors: Cary Reich, Menlo Park, CA (US); Eugene de Juan, Jr., Menlo Park, CA (US); Yair Alster, Menlo Park, CA (US)

(73) Assignee: ForSight Labs, LLC, Menlo Park, CA (US)

(*) Notice: Subject to any disclaimer, the term of this patent is extended or adjusted under 35 U.S.C. 154(b) by 0 days.

(21) Appl. No.: 14/067,839

(22) Filed: Oct. 30, 2013

(65) Prior Publication Data
US 2014/0058507 A1 Feb. 27, 2014

Related U.S. Application Data

(63) Continuation of application No. 13/366,165, filed on Feb. 3, 2012, now abandoned.
(Continued)

(51) Int. Cl.
*A61F 2/16* (2006.01)

(52) U.S. Cl.
CPC .......... *A61F 2/1624* (2013.01); *A61F 2/1635* (2013.01); *A61F 2/1602* (2013.01);
(Continued)

(58) Field of Classification Search
CPC .... A61F 2/1613; A61F 2/1616; A61F 2/1624; A61F 2/1629; A61F 2/1635; A61F 2/1648; A61F 2/1651; A61F 2002/1681–2002/1686; A61F 2002/1697; A61F 2220/0008; A61F 2220/0025–2220/0066; A61F 2250/0004–2250/001; A61F 2250/0018; A61F 2250/0053; A61F 2250/0065; A61F 2250/0091
(Continued)

(56) References Cited

U.S. PATENT DOCUMENTS

| | | |
|---|---|---|
| 4,159,546 A | 7/1979 | Shearing |
| 4,373,218 A | 2/1983 | Schachar |

(Continued)

FOREIGN PATENT DOCUMENTS

| | | |
|---|---|---|
| EP | 1917932 A1 | 5/2008 |
| EP | 1932492 A1 | 6/2008 |

(Continued)

*Primary Examiner* — Paul Prebilic
(74) *Attorney, Agent, or Firm* — Mintz Levin Cohn Ferris Glovsky and Popeo, P.C.

(57) ABSTRACT

Described herein are intraocular lenses and methods of implantation. In one aspect, the lens includes a shape changing optical element; a force translation element having a first end region coupled to the optical element and a second end region extending towards a ciliary structure, and an attachment portion coupled to the second end region of the force translation element and configured to contact the ciliary structure. The force translation element is configured to functionally transmit movements of the ciliary structure into a force exerted upon the optical element to effect an accommodating and a disaccommodating change of the optical element.

25 Claims, 10 Drawing Sheets

Related U.S. Application Data

(60) Provisional application No. 61/439,767, filed on Feb. 4, 2011.

(52) U.S. Cl.
CPC ..... *A61F 2/1648* (2013.01); *A61F 2250/0018* (2013.01); *F04C 2270/041* (2013.01)

(58) Field of Classification Search
USPC ........................................................ 623/6.52
See application file for complete search history.

(56) References Cited

U.S. PATENT DOCUMENTS

| | | | |
|---|---|---|---|
| 4,685,921 A | 8/1987 | Peyman | |
| 4,731,078 A | 3/1988 | Stoy et al. | |
| 4,734,095 A | 3/1988 | Siepser | |
| 4,769,035 A | 9/1988 | Kelman | |
| 4,782,820 A | 11/1988 | Woods | |
| 4,787,903 A | 11/1988 | Grendahl | |
| 4,816,030 A | 3/1989 | Robinson | |
| 4,816,031 A | 3/1989 | Pfoff | |
| 4,842,601 A | 6/1989 | Smith | |
| 4,888,012 A | 12/1989 | Horn et al. | |
| 4,892,543 A | 1/1990 | Turley | |
| 4,932,966 A * | 6/1990 | Christie et al. | 623/6.13 |
| 4,957,505 A | 9/1990 | McDonald | |
| 5,066,301 A | 11/1991 | Wiley | |
| 5,171,266 A | 12/1992 | Wiley et al. | |
| RE34,424 E | 10/1993 | Walman | |
| 5,275,623 A | 1/1994 | Sarfarazi | |
| 5,288,293 A | 2/1994 | O'Donnell, Jr. | |
| 5,443,506 A | 8/1995 | Garabet | |
| 5,489,302 A * | 2/1996 | Skottun | 623/6.13 |
| 5,607,472 A | 3/1997 | Thompson | |
| 5,684,637 A | 11/1997 | Floyd | |
| 5,766,245 A | 6/1998 | Fedorov et al. | |
| 5,774,273 A | 6/1998 | Bornhorst | |
| 5,800,806 A * | 9/1998 | Yamamoto | 424/76.1 |
| 5,932,205 A | 8/1999 | Wang et al. | |
| 6,013,101 A * | 1/2000 | Israel | 623/6.43 |
| 6,027,531 A | 2/2000 | Tassignon | |
| 6,096,078 A | 8/2000 | McDonald | |
| 6,117,171 A | 9/2000 | Skottun | |
| 6,120,538 A | 9/2000 | Rizzo, III et al. | |
| 6,143,315 A | 11/2000 | Wang et al. | |
| 6,188,526 B1 | 2/2001 | Sasaya et al. | |
| 6,228,115 B1 | 5/2001 | Hoffmann et al. | |
| 6,261,321 B1 | 7/2001 | Kellan | |
| 6,299,641 B1 | 10/2001 | Woods | |
| 6,387,126 B1 | 5/2002 | Cumming | |
| 6,443,985 B1 | 9/2002 | Woods | |
| 6,450,642 B1 | 9/2002 | Jethmalani et al. | |
| 6,493,151 B2 * | 12/2002 | Schachar | G02B 3/14 359/666 |
| 6,506,212 B2 | 1/2003 | Zhou et al. | |
| 6,552,860 B1 | 4/2003 | Alden | |
| 6,558,420 B2 | 5/2003 | Green | |
| 6,592,621 B1 | 7/2003 | Domino | |
| 6,645,246 B1 | 11/2003 | Weinschenk, III et al. | |
| 6,730,123 B1 | 5/2004 | Klopotek | |
| 6,733,122 B1 | 5/2004 | Feurer et al. | |
| 6,749,634 B2 | 6/2004 | Hanna | |
| 6,818,017 B1 | 11/2004 | Shu | |
| 6,836,374 B2 | 12/2004 | Esch et al. | |
| 6,851,804 B2 | 2/2005 | Jethmalani et al. | |
| 6,855,164 B2 | 2/2005 | Glazier | |
| 6,860,601 B2 | 3/2005 | Shadduck | |
| 6,930,838 B2 | 8/2005 | Schachar | |
| 6,935,743 B2 | 8/2005 | Shadduck | |
| 6,966,649 B2 | 11/2005 | Shadduck | |
| 7,008,449 B2 | 3/2006 | Willis et al. | |
| 7,025,783 B2 | 4/2006 | Brady et al. | |
| 7,060,094 B2 | 6/2006 | Shahinpoor et al. | |
| 7,068,439 B2 | 6/2006 | Esch et al. | |
| 7,097,660 B2 | 8/2006 | Portney | |
| 7,118,596 B2 | 10/2006 | Zadno-Azizi et al. | |
| 7,118,597 B2 | 10/2006 | Miller et al. | |
| 7,122,053 B2 | 10/2006 | Esch | |
| 7,217,288 B2 | 5/2007 | Esch et al. | |
| 7,220,279 B2 | 5/2007 | Nun | |
| 7,229,476 B2 * | 6/2007 | Azar | 623/6.26 |
| 7,247,168 B2 | 7/2007 | Esch et al. | |
| 7,256,943 B1 | 8/2007 | Kobrin et al. | |
| 7,261,737 B2 | 8/2007 | Esch et al. | |
| 7,278,739 B2 | 10/2007 | Shadduck | |
| 7,293,873 B2 | 11/2007 | Dai et al. | |
| 7,341,599 B1 | 3/2008 | Peyman | |
| 7,369,321 B1 | 5/2008 | Ren et al. | |
| 7,381,221 B2 | 6/2008 | Lang et al. | |
| 7,384,429 B2 | 6/2008 | Hanna | |
| 7,438,723 B2 | 10/2008 | Esch | |
| 7,453,646 B2 | 11/2008 | Lo | |
| 7,485,144 B2 | 2/2009 | Esch | |
| 7,601,169 B2 | 10/2009 | Phillips | |
| 7,615,056 B2 | 11/2009 | Ayton et al. | |
| 7,637,947 B2 | 12/2009 | Smith et al. | |
| 7,675,686 B2 | 3/2010 | Lo et al. | |
| 7,713,299 B2 | 5/2010 | Brady et al. | |
| 7,753,953 B1 | 7/2010 | Yee | |
| 7,763,069 B2 | 7/2010 | Brady et al. | |
| 7,776,088 B2 | 8/2010 | Shadduck | |
| 7,854,764 B2 | 12/2010 | Ben Nun | |
| 7,857,850 B2 | 12/2010 | Mentak et al. | |
| 7,883,540 B2 | 2/2011 | Niwa et al. | |
| 7,985,253 B2 | 7/2011 | Cumming | |
| 7,988,285 B2 | 8/2011 | Sandstedt et al. | |
| 8,018,658 B2 | 9/2011 | Lo | |
| 8,034,106 B2 | 10/2011 | Mentak et al. | |
| 8,158,712 B2 | 4/2012 | Your | |
| 8,314,927 B2 | 11/2012 | Choi et al. | |
| 8,343,216 B2 | 1/2013 | Brady et al. | |
| 8,377,125 B2 | 2/2013 | Kellan | |
| 8,414,646 B2 | 4/2013 | De Juan, Jr. et al. | |
| 8,663,235 B2 | 3/2014 | Tassignon | |
| 8,668,734 B2 | 3/2014 | Hildebrand et al. | |
| 8,851,670 B2 | 10/2014 | Dai et al. | |
| 8,900,298 B2 | 12/2014 | Anvar et al. | |
| 8,956,408 B2 | 2/2015 | Smiley et al. | |
| 8,968,396 B2 | 3/2015 | Matthews et al. | |
| 8,974,526 B2 | 3/2015 | Bogaert | |
| 9,005,282 B2 | 4/2015 | Chang et al. | |
| 9,044,317 B2 | 6/2015 | Hildebrand et al. | |
| 9,114,005 B2 | 8/2015 | Simonov et al. | |
| 9,326,846 B2 | 5/2016 | Devita Gerardi et al. | |
| 9,421,089 B2 | 8/2016 | Zadno-Azizi | |
| 2001/0001836 A1 * | 5/2001 | Cumming | A61F 2/1629 623/6.37 |
| 2003/0060878 A1 | 3/2003 | Shadduck | |
| 2003/0149480 A1 * | 8/2003 | Shadduck | 623/6.41 |
| 2003/0171809 A1 | 9/2003 | Phillips | |
| 2004/0006387 A1 * | 1/2004 | Kelman | 623/6.36 |
| 2004/0034417 A1 | 2/2004 | Heyman | |
| 2004/0039446 A1 * | 2/2004 | McNicholas | 623/6.37 |
| 2004/0082993 A1 | 4/2004 | Woods | |
| 2004/0082995 A1 | 4/2004 | Woods | |
| 2004/0111153 A1 * | 6/2004 | Woods et al. | 623/6.37 |
| 2004/0162612 A1 * | 8/2004 | Portney et al. | 623/6.34 |
| 2004/0169820 A1 | 9/2004 | Dai et al. | |
| 2004/0237971 A1 | 12/2004 | Radhakrishnan et al. | |
| 2005/0021138 A1 | 1/2005 | Woods | |
| 2005/0060032 A1 | 3/2005 | Magnante et al. | |
| 2005/0065534 A1 | 3/2005 | Hohl | |
| 2005/0113914 A1 | 5/2005 | Miller et al. | |
| 2005/0125059 A1 | 6/2005 | Pinchuk et al. | |
| 2005/0137703 A1 | 6/2005 | Chen | |
| 2005/0251253 A1 | 11/2005 | Gross | |
| 2006/0047340 A1 * | 3/2006 | Brown | A61F 2/1602 623/6.13 |
| 2006/0100701 A1 | 5/2006 | Esch et al. | |
| 2006/0259138 A1 | 11/2006 | Peyman | |
| 2007/0100444 A1 | 5/2007 | Brady et al. | |
| 2007/0123982 A1 | 5/2007 | Yablonski et al. | |
| 2007/0129798 A1 | 6/2007 | Chawdhary | |

(56) References Cited

U.S. PATENT DOCUMENTS

| | | |
|---|---|---|
| 2007/0129800 A1 | 6/2007 | Cumming |
| 2008/0046075 A1 | 2/2008 | Esch et al. |
| 2008/0046076 A1* | 2/2008 | Rombach .................... 623/6.34 |
| 2008/0097459 A1 | 4/2008 | Kammerlander et al. |
| 2008/0103592 A1 | 5/2008 | Maloney |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0288066 A1 | 11/2008 | Cumming |
| 2009/0012609 A1* | 1/2009 | Geraghty et al. ............ 623/6.11 |
| 2009/0171458 A1 | 7/2009 | Kellan et al. |
| 2009/0234449 A1 | 9/2009 | De Juan, Jr. et al. |
| 2009/0292355 A1 | 11/2009 | Boyd et al. |
| 2010/0094415 A1* | 4/2010 | Bumbalough ............... 623/6.51 |
| 2010/0121444 A1* | 5/2010 | Ben Nun .............. A61F 2/1635 623/6.34 |
| 2011/0054600 A1* | 3/2011 | Bumbalough ........ A61F 2/1635 623/6.39 |
| 2011/0071628 A1 | 3/2011 | Gross et al. |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2015/0257874 A1 | 9/2015 | Hildebrand et al. |

FOREIGN PATENT DOCUMENTS

| | | |
|---|---|---|
| JP | 2005169131 A | 6/2005 |
| JP | 2005533611 A | 11/2005 |
| JP | 2009532176 A | 9/2009 |
| JP | 2011500270 A | 1/2011 |
| WO | WO-03/000154 A2 | 1/2003 |
| WO | WO-03/017867 A2 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005/057272 A2 | 6/2005 |
| WO | WO-2005/082285 A1 | 9/2005 |
| WO | WO-2007/113832 A2 | 10/2007 |
| WO | WO-2007/117476 A2 | 10/2007 |
| WO | WO-2008/031231 A1 | 3/2008 |
| WO | WO-2009/055099 A1 | 4/2009 |
| WO | WO-2010/010565 A2 | 1/2010 |
| WO | WO-2012/006186 A2 | 1/2012 |
| WO | WO-2012/023133 A1 | 2/2012 |
| WO | WO-2012/067994 A2 | 5/2012 |
| WO | WO-2013/016804 A1 | 2/2013 |

* cited by examiner

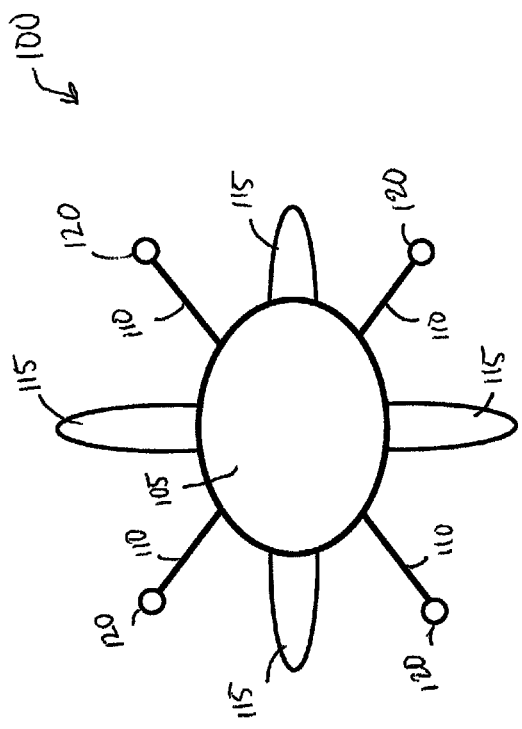
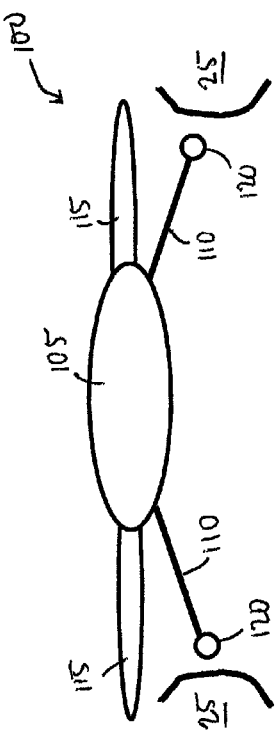
Figure 5A
Figure 5B

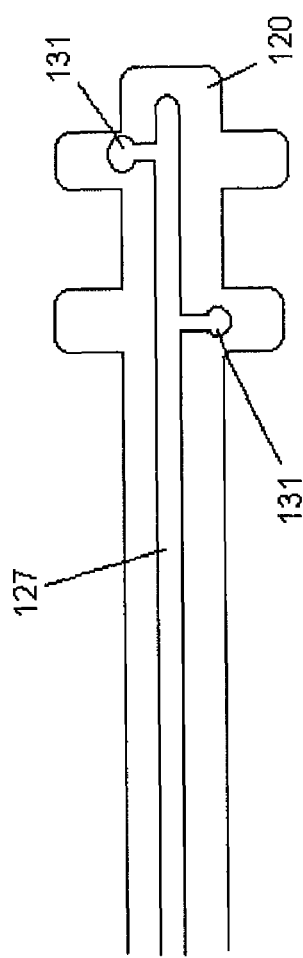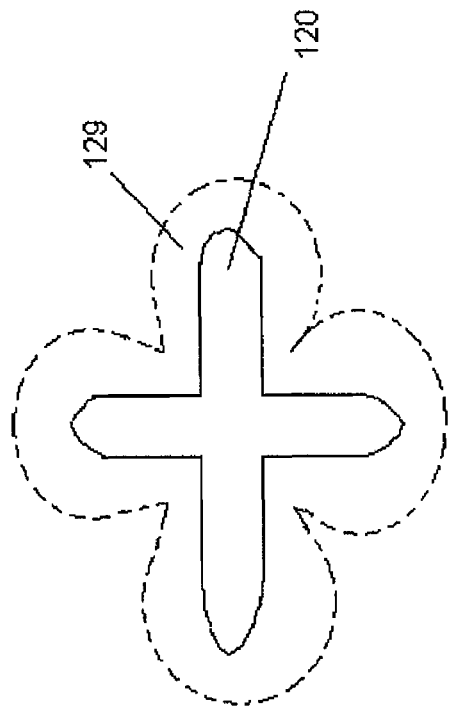
FIG. 7A
FIG. 7B

INTRAOCULAR ACCOMMODATING LENS AND METHODS OF USE

REFERENCE TO PRIORITY DOCUMENT

This application is a continuation of U.S. patent application Ser. No. 13/366,165, entitled "Intraocular Accommodating Lens and Methods of Use," filed Feb. 3, 2012, now abandoned, which claims the benefit of priority to U.S. Provisional Patent Application Ser. No. 61/439,767, entitled "Intraocular Accommodating Lens and Methods of Use," filed Feb. 4, 2011. Priority of the aforementioned filing dates is hereby claimed and the disclosures of the applications are hereby incorporated by reference in their entirety.

BACKGROUND

The present disclosure relates generally to the field of ophthalmics, more particularly to ophthalmic devices, including intraocular lenses (IOLs) such as accommodating intraocular lenses.

A healthy young human eye can focus an object in far or near distance, as required. The capability of the eye to change back and forth from near vision to far vision is called accommodation. Accommodation occurs when the ciliary muscle contracts to thereby release the resting zonular tension on the equatorial region of the capsular bag. The release of zonular tension allows the inherent elasticity of the lens capsule to alter to a more globular or spherical shape, with increased surface curvatures of both the anterior and posterior lenticular surfaces.

The human lens can be afflicted with one or more disorders that degrade its functioning in the vision system. A common lens disorder is a cataract which is the opacification of the normally clear, natural crystalline lens matrix. The opacification can result from the aging process but can also be caused by heredity or diabetes. In a cataract procedure, the patient's opaque crystalline lens is replaced with a clear lens implant or IOL.

In conventional extracapsular cataract surgery, the crystalline lens matrix is removed leaving intact the thin walls of the anterior and posterior capsules together with zonular ligament connections to the ciliary body and ciliary muscles. The crystalline lens core is removed by phacoemulsification through a curvilinear capsularhexis i.e., the removal of an anterior portion of the capsular sac.

After a healing period of a few days to weeks, the capsular sac effectively shrink-wraps around the IOL due to the capsularhexis, the collapse of the walls of the sac and subsequent fibrosis. Cataract surgery as practiced today causes the irretrievable loss of most of the eye's natural structures that provide accommodation. The crystalline lens matrix is completely lost and the integrity of the capsular sac is reduced by the capsularhexis. The "shrink-wrap" of the capsular sac around the IOL can damage the zonule complex, and thereafter the ciliary muscles may atrophy. Thus, conventional IOUs, even those that profess to be accommodative, may be unable to provide sufficient axial lens spatial displacement along the optical axis or lens shape change to provide an adequate amount of accommodation for near vision.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the sulcus and are non-accommodating.

SUMMARY

In one aspect, described herein is an intraocular lens including a shape changing optical element; a force translation element having a first end region coupled to the optical element and a second end region extending towards a ciliary structure, and an attachment portion coupled to the second end region of the force translation element and configured to contact the ciliary structure. The force translation element is configured to functionally transmit movements of the ciliary structure into a force exerted upon the optical element to effect an accommodating and a disaccommodating change of the optical element.

The force translation element can be customized for fit during implantation. The mechanism for customizing the fit can include sliding, twisting, turning, cutting, rolling, expanding, bending, and applying energy to the force translation element. The force translation element can be coated with an expandable material. At least one of the optical element, the force translation element, and the attachment portion can be coated with an agent having biological activity such as heparin, a steroid and rapamycin. The first end region of the force translation element can be coupled to an equator of the optical element. A plurality of force translation elements can be coupled near an equator of the optical element.

The attachment portion can be configured to contact the ciliary structure. The attachment portion can be configured to abut and not penetrate the ciliary structure. The ciliary structure can be the ciliary muscle, the ciliary body, a ciliary process, and a zonule. The attachment portion can be formed of an elastic material. The attachment portion can include one or more rods. The one or more rods can be curved. The attachment portion can include a three dimensional element that fills a space adjacent the ciliary structure. The attachment portion can include a fillable element. The attachment portion can include a glue, hydrogel or fixation material. The attachment portion can elicit a healing response in the ciliary structure to induce soft tissue integration of the attachment portion.

The optical element can have a power in the range of about ±3 diopters to about ±5 diopters. The accommodating change of the optical element can include a change from an ovoid shape to a more spherical shape. The accommodating change of the optical element can include a change in spatial configuration along the optical axis in an anterior direction. The force translation element can be formed of a material generally harder than a material of the optical element. The second lens can be positioned within the capsular bag of the eye. The optical element can be positioned anterior to the second lens. The optical element can be positioned within the capsular bag of the eye. The optical element can be positioned posterior to the iris. The optical element can be positioned anterior to the iris. The second lens can include an implanted intraocular lens.

The lens can further include a haptic coupled to and extending outward from the optical element. The haptic can be positioned within a sulcus. The force translation element can be coupled to the haptic. The force translation element can be coupled to the ciliary body to push on the optical element.

The force translation element can be coupled to the ciliary body to pull on the optical element. The accommodating and disaccommodating change can include a shape change effected over the entire surface of the optical element. The accommodating and disaccommodating change can include a shape change effected over a portion of the optical element. The portion can preferentially bulge upon an accommodating change. The shape change effected over a portion can be due to a difference in modulus of the portion of the optical element compared to the modulus of another portion of the optical element. A center region of the optical element can include a lower modulus material than an outer region of the optical element. The lower modulus material can give way causing a bulge and a change in dioptric effect.

These general and specific aspects may be implemented using the devices, methods, and systems or any combination of the devices, methods and systems disclosed herein. Other features and advantages should be apparent from the following description of various embodiments, which illustrate, by way of example, the principles of the described subject matter.

BRIEF DESCRIPTION OF THE DRAWINGS

FIGS. 5A-5B depict schematic top and side views, respectively of another embodiment of a lens having haptics and force translation elements;

FIGS. 7A-7B depict schematic views of additional embodiments of a lens having a hydrogel coating.

Figure 1:
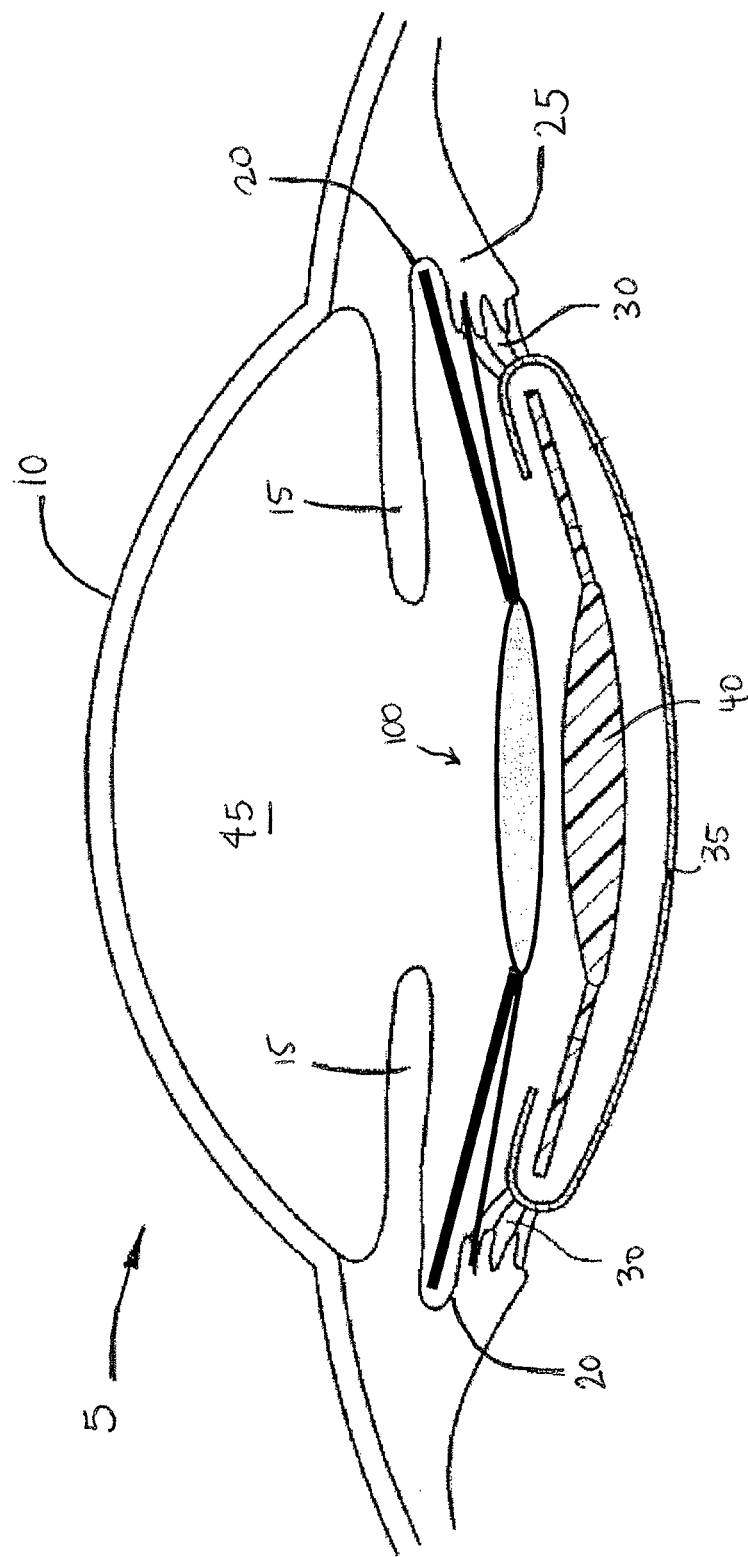
FIG. 1 depicts a cross-sectional, schematic view of an eye showing an embodiment of an intraocular lens implanted anterior to another intraocular lens implanted in the capsular bag.

It should be appreciated that the drawings herein are exemplary only and are not meant to be to scale.

DETAILED DESCRIPTION

There is a need for improved methods and devices for the treatment of presbyopia in phakic and pseudophakic patients. The intraocular lenses described herein can be switched back and forth repeatedly between accommodation to disaccommodation, just as in a young accommodative natural eye.

The term shape changing optical element refers to an optical element that is made of material that enables the optical element to alter its shape, e.g., become one of more spherical in shape, thicker to focus on a closer object; or become more ovoid in shape, thinner to focus on a more distant and thus alter the optical element's respective optics (alter the dioptric power of the resulting optical element). The shape change can be effected over the entire surface of the optical element, or just over a portion of the optical element, such as by having a preferential change or "bulge" in a portion of the optical element. This can be achieved by varying the modulus of portions of the optical element. For example, the center region may be a lower modulus material than the outer region of the optical element in which case when the ciliary body accommodates and the force will be translated to the center of the optical element preferentially to cause a "bulge" that will provide the desired dioptric effect.

Alternatively, the optical element may be a dual optic that is designed to translate relative to each other to increase or decrease the dioptric power of the system.

The term accommodating shape refers to the shape of the optical element when at least one of the contraction of the ciliary muscle of the mammalian eye, the lower tension of the zonules of the mammalian eye and a decrease in the vitreous pressure in the eye occur to effect a focusing upon a closer object. An accommodating shape is generally more spherical than the disaccommodating shape.

The term disaccommodating shape refers to the shape of the optical element when at least one of the relaxation of the ciliary muscle of the mammalian eye, the higher tension of the zonules of the mammalian eye and an increase in the vitreous pressure in the eye occur to effect a focusing upon a more distant object. A disaccommodating shape is generally more ovoid than the accommodating shape.

The term diopter (D) refers to the reciprocal of the focal length of a lens in meters. For example, a 10 D lens brings parallel rays of light to a focus at ($\frac{1}{10}$) meter. After a patient's natural crystalline lens has been surgically removed, surgeons usually follow a formula based on their own personal preference to calculate a desirable diopter power (D) for the selection of an IOL for the patient to correct the patient's preoperational refractive error. For example, when a myopia patient with −10 D undergoes cataract surgery and IOL implantation, the patient can see at a distance well enough even without glasses. Generally, this is because the surgeon has taken the patient's −10 D near-sightedness into account when choosing an IOL for the patient.

The lenses described herein can mechanically or functionally interact with eye tissues typically used by a natural lens during accommodation and disaccommodation such as the ciliary body, ciliary processes, and the zonules, to effect accommodation and disaccommodation of the implanted lens. The forces generated by these tissues are functionally translated to the optical element of the implanted lens causing a power change to allow a phakic or pseudophakic patient to more effectively accommodate.

The intraocular lenses described herein can be implanted in the eye to replace a diseased, natural lens. The intraocular lenses described herein can also be implanted as a supplement of a natural lens (phakic patient) or an intraocular lens previously implanted within a patient's capsular bag (pseudophakic patient). The lenses described herein can be used in combination with intraocular lenses described in U.S. Patent Publication Nos. 2009/0234449 and 2009/0292355, which are each incorporated by reference herein in their entirety. As such, the lenses described herein can be used independently or as so-called "piggyback" lenses. Piggyback lenses can be used to correct residual refractive errors in phakic or pseudophakic eyes. The primary IOL used to replace the natural lens is generally thicker and has a power that can be in the range of ±20 D. The thicker, larger power lenses generally have less accommodation. In contrast, the supplemental lens need not possess a full range of diopters (D). The supplemental lens can be relatively thin compared to the primary IOL and can undergo more accommodation. Shape change and movement of the thinner lens is generally more easily accomplished relative to a thick primary lens. It should be appreciated, however, that the lenses described herein can be used independently and need not be used in combination as piggyback lenses with the natural lens or an implanted IOL.

FIG. 1 depicts a cross-sectional view of an eye 5 including the cornea 10, iris 15, sulcus 20, ciliary body 25, ciliary processes 27, zonules 30 and the capsular bag 35 including an IOL 40 implanted in the capsular bag 35. A lens 100 is shown positioned within the sulcus 20 anterior to the IOL 40. It should be appreciated that although the lens 100 is shown positioned within the sulcus 20 and posterior to the iris 15 that it can also be positioned anterior to the iris 15 within the anterior chamber 45. The lens 100 can also be positioned within the capsular bag 35 just in front of the previously implanted IOL 40 or natural lens.

Figure 2:
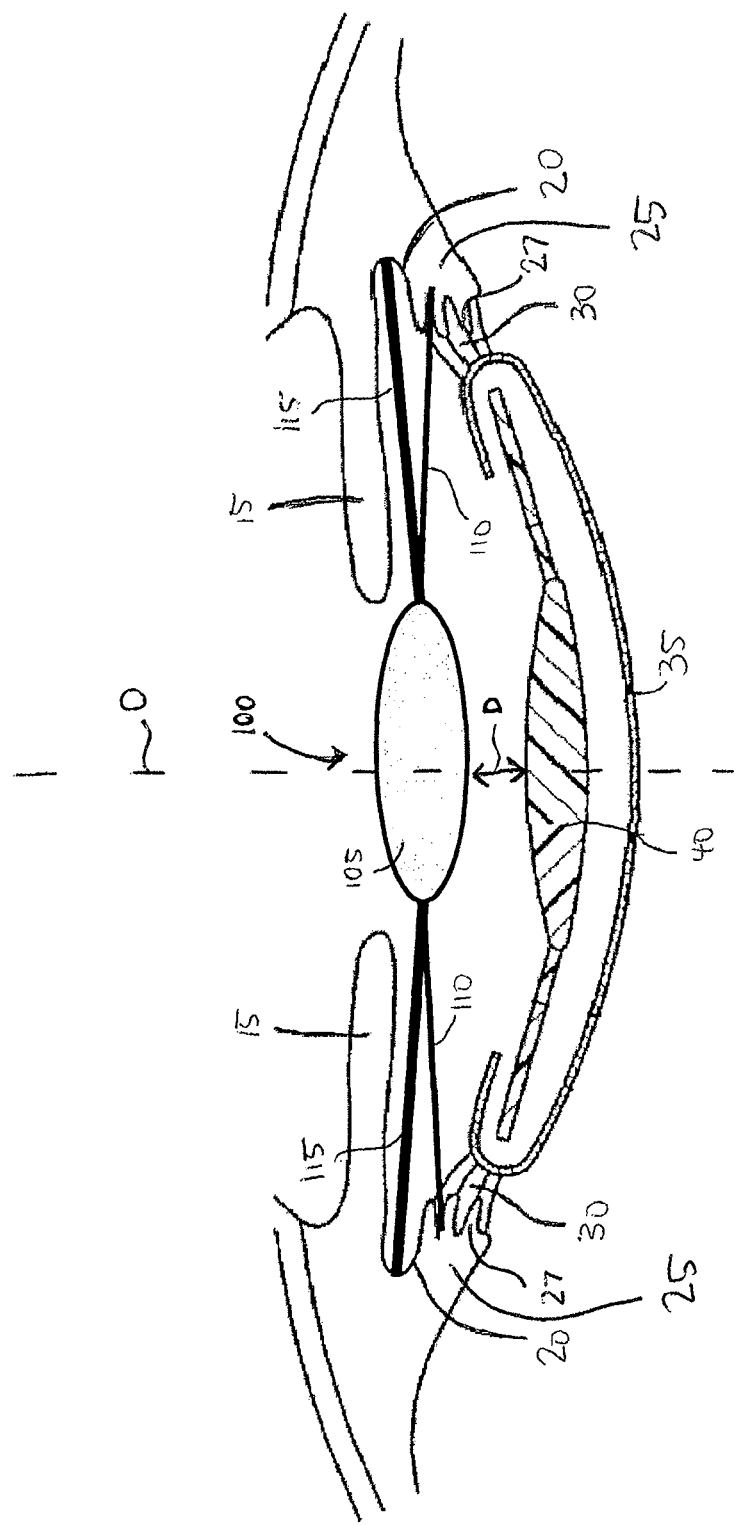
FIG. 2 depicts a cross-sectional, schematic view of the lens of FIG. 1 during accommodation.

The lens 100 can include a central optical element 105 and at least two force translation elements 110 extending outward from the optical element 105 (see FIG. 2). The optical element 105 can be an adjustable lens such that the optical properties can be manipulated after implantation, as will be described in more detail below. The force translation elements 110 can functionally couple with at least one of the ciliary structures such as the ciliary body 25, ciliary processes 27, and/or the zonules 30 such that movements of these tissues during accommodation and disaccommodation are translated to the optical element 105 via the force translation elements 110 to cause at least a change in shape or change in position of the optical element 105. The lens 100 can further include at least two haptics 115 coupled to and extending outward from the optical element 105. The haptics 115 can be positioned within the sulcus 20 to further aid in the anchoring of the lens in the eye.

FIG. 2 depicts a cross-sectional, schematic view of the lens 100 during accommodation. The ciliary body 25 is a generally circular structure. The ciliary muscle is a sphincter shaped like a doughnut. In natural circumstances, when the eye is viewing an object at a far distance, the ciliary muscle within the ciliary body 25 relaxes and the inside diameter of the ciliary muscle gets larger. The ciliary processes 27 pull on the zonules 30, which in turn pull on the lens capsule 35 around its equator. This causes a natural lens to flatten or to become less convex, which is called disaccommodation. During accommodation, the muscles of the ciliary body 25 contract and the inside diameter of the ciliary muscle gets smaller. The ciliary processes 27 release the tension on the zonules 30 and the lens takes on its natural, more convex shape such that the eye can focus at near distance.

Without limiting this disclosure to any particular theory or mode of operation, the eye is believed to act on the implanted intraocular lenses described herein as follows. The force translation elements 110 are implanted such that they are in contact with at least one of the ciliary structures (i.e. zonules 30, ciliary processes 27 and/or ciliary body 25). The contraction of the ciliary muscle and inward movement of the tissues towards the optical axis O applies a force against the force translation elements 110 (see FIG. 2). The force translation elements 110 transfer the force to the optical element 105, which can take on a more spherical shape suitable for near vision. This contraction of the ciliary muscle and inward movement of the ciliary body 25 can also result in a change in the spatial configuration of the lens 100 such that it axially displaces along the optical axis O forwardly in an anterior direction (distance D) relative to the natural lens or a previously implanted IOL 40. Both the more spherical shape and the anterior movement away from IOL 40 can cause an increase in power needed for accommodation and near vision focus.

As mentioned, the force translation elements 110 can be configured to cooperate with at least one of the ciliary body 25, ciliary processes 27, or the zonules 30 to change the shape of the optical element 105. It should be appreciated that the vitreous pressure in the eye can also be involved in the accommodating shape of the optical element 105. Further, if the lens 100 is implanted anterior to the iris 15, for example within the anterior chamber 45, the structures of the anterior chamber angle can also affect the accommodating shape change of the optical element 105.

Figure 3A:
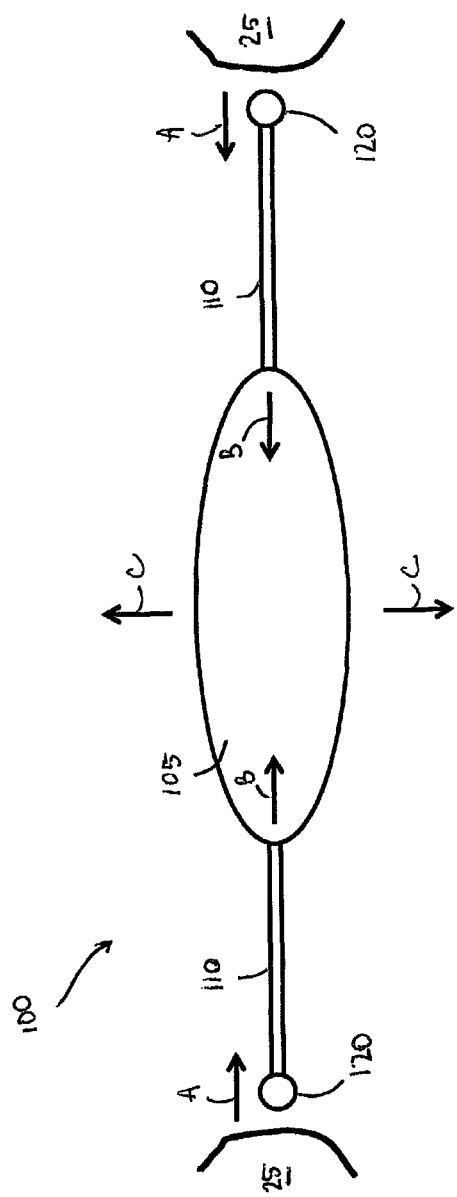
FIG. 3A depicts a schematic view of an embodiment of a lens.
Figure 3B:
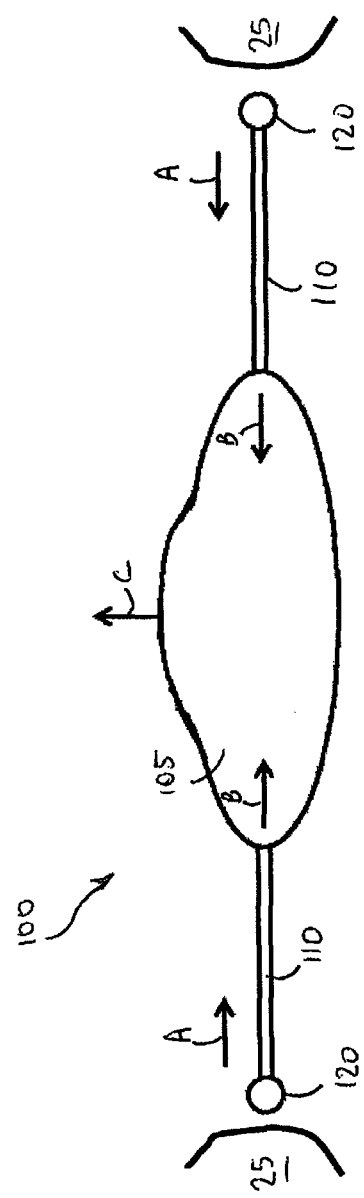
FIG. 3B depicts a schematic view of another embodiment of a lens.

FIGS. 3A-3B depict an embodiment of an intraocular lens 100 having an optical element 105 and two force translation elements 110 extending outward from near the equator of optical element 105. It should be appreciated that the force translation elements 110 can also extend outward from other regions of the optical element 105. For example, the force translation element 110 can be coupled nearer to one or more of the poles of the optical element 105. The force translation elements 110 can be coupled to the optical element 105 or the force translation elements 110 can be coupled to and extend from haptics 115, if present. It should also be appreciated that the lens 100 can have more than two force translation elements 110 such as three, four, five or more force translation elements 110. In one aspect, the force translation elements 110 can extend from the optical element 105 on opposing sides of the optical axis O.

When implanted in the eye, an end of the force translation elements 110 can be positioned adjacent the ciliary body 25 on either side of the eye. The force translation elements 110 can be adapted to translate force applied by the adjacent tissues to the optical element 105 to cause a shape change or a relative spatial change or both. The force translation elements 110 can be generally formed of a harder material than that of the optical element 105. A change in hardness or durometer can be accomplished via a change in material. For example, a higher durometer material can be used for the force translation elements 110 than the material used for the optical element 105. For example, the force translation elements 110 can be made from silicone and the optical element 105 can be made from a softer hydrogel. Alternatively, the materials of the force translation elements 110 and the optical element 105 can be the same, but the hardness different. Hardness can be determined or quantized using the Shore A or Shore D scale. The various materials considered herein for forming the components of the lens 100 are discussed in more detail below.

As mentioned, the optical element 105 can change to a more spherical shape during accommodation upon narrowing of the inside diameter of the ciliary body 25 by mechanically and functionally connecting with the movement of one or more of the ciliary tissues. As shown in FIG. 3A, contraction of the muscles of the ciliary body 25 can create a force in the direction of arrows A, which is then applied to the force translation elements 110. The force translation elements 110 translate that force to the optical element 105 (arrows B). Depending on the design of the optical element 105, the optical element 105 can change shape, for example, along arrows C shown in FIGS. 3A and 3B into a more spherical, accommodated shape to view a near object. If a far object is to be viewed, the optical element 105 can return to its resting, disaccommodating shape, which is more flat upon relaxation of the ciliary body 25 and return to its posterior-most resting configuration decreasing its effective power because the force translation elements 115 are no longer being urged inward by the surrounding tissues.

The optical element 105 can be designed to include a variety of features that cause an accommodative change in power. The optical element 105 can include internal cleavage planes to cause bulging in the center of the optical element 105 when the ciliary body 25 and its associated tissues are in the accommodative position increasing the power in the center of the optical element 105 (as shown in FIG. 3B). The optical element 105 can also be fluid-filled such that movement of the ciliary body 25 and its associated tissues can cause the fluid to move and bulge near the center of the optical element 105 increasing its power. The configuration of the optical element 105 can vary as is described in U.S. Patent Publication Nos. 2009/0234449 and 2009/0292355, which are each incorporated by reference herein in their entirety.

Figure 3C:
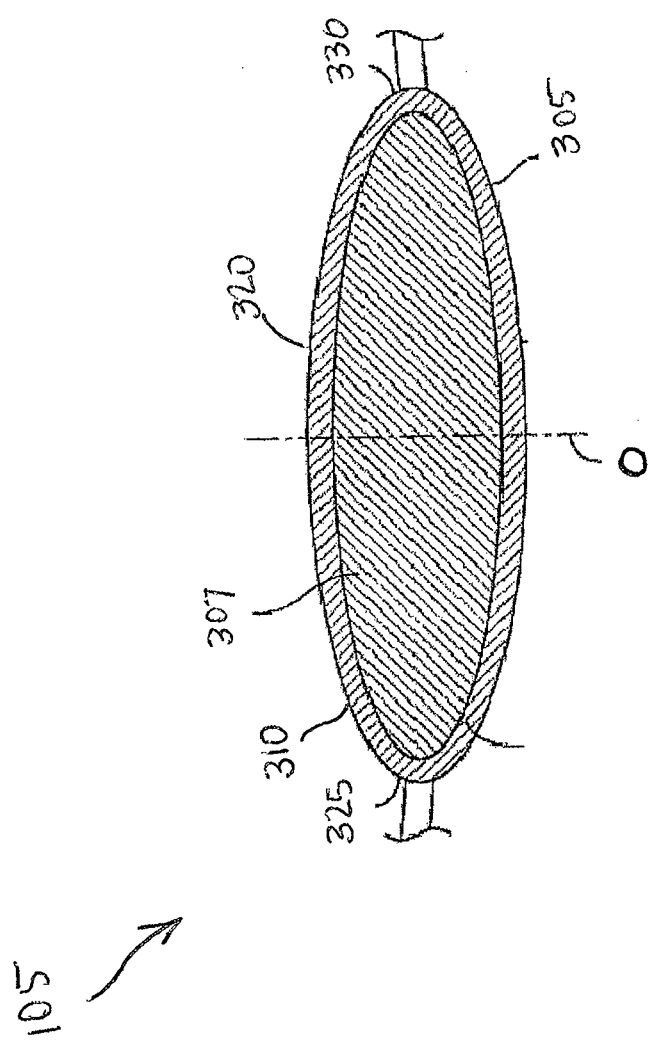
FIG. 3C depicts a cross-sectional view of the optical element of the lens of FIG. 3A.

As an example, FIG. 3C illustrates an optical element 105 having an outer lens portion 305 and a core lens portion 307. The outer lens portion 305 can be structured to include a center section 320 that can have a reduced thickness or hardness. The center section 320 can surround the optical axis O of the optical element 105 and can be located on or near the anterior face 310 thereof. When the lens 100, and in particular the optical element 105, is compressed, for example by an inward force at peripheral regions 325 and 330 applied by the force translation elements 110, the optical element 105 can be reshaped by an outward bowing of the anterior face 310. This inward force by the force translation elements 110 is due to the compressive force applied to the force translation elements 110 by at least one of the ciliary body 25, ciliary processes 27, or zonules 30 depending on how the lens 100 is implanted.

Figure 3D:
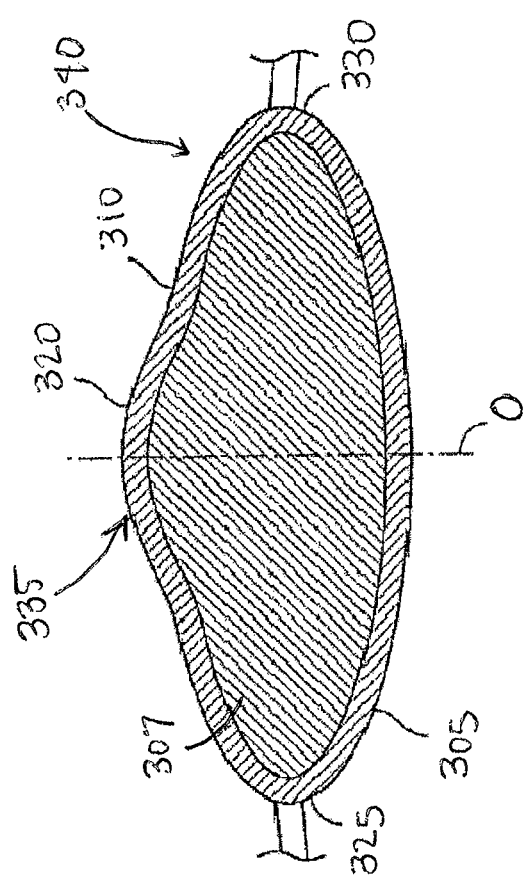
FIG. 3D depicts a cross-sectional view of the optical element of the lens of FIG. 3B.

As shown in FIG. 3D, the outward bowing or reshaping can be especially pronounced at region 335. This can be due to a reduced thickness of the outer lens portion 305 at center section 320. The reduced thickness can be relatively more prone to give way from the internal pressure of the core lens portion 307 upon inward force applied at the peripheral regions 325, 330. The core lens portion 307 can extend forward, as seen for example in the central region 335 in FIG. 3D. The center section 320 can also include a material of reduced hardness or increased elasticity to be more prone to give way from the internal pressure.

The extended central region 335 of optical element 105 can provide near vision correction power. The remainder of the outer portion 305 outside the center section 320 can have a greater thickness that can be more resistant to reshaping under such compression at the peripheral regions 325, 330. As such, the annular region 340 of optical element 105 extending radially outward of center section 335 can continue to provide distance vision correction power. The regions 335 and 340 of optical element 105, under compression, can provide both near and distance vision correction powers, respectively. In other words, the anterior surface 310 of optical element 105 can be a multifocal surface when the optical element 105 is under compression. In contrast, when the optical element 105 is in the resting position as shown in FIG. 3C, the anterior surface 310 can be a monofocal surface.

FIG. 3D illustrates an alternative embodiment of the lens 100, which is substantially the same as that shown in FIG. 3C, except for a different construction of the outer portion 305. The center section 320 can be made of a material that is relatively more susceptible to outward bowing than is the peripheral region surrounding it. The center section 320 can be injection molded in combination with the peripheral regions surrounding it to provide a relatively seamless and uninterrupted anterior face 310, at least in the rest position of the lens 100. When the peripheral regions 325 and 330 are squeezed towards the optical axis O, the core lens portion 307 can be placed in compression thus forcing the center section 320 in the anterior direction as shown in the extended region 335. The material of the outer portion 305 can be generally consistent, though the center section 320 can have a different stiffness or elasticity that causes it to bow outward farther than the surrounding region.

The extent to which central region 335 extends forwardly, and therefore the magnitude of the near vision correction power obtainable by the optical element 105, can depend on a number of factors, such as the relative thickness, hardness, stiffness, elasticity etc. of center section 320, the overall structure of the outer portion 305 and/or the inner portion 307, the material of construction of the outer portion and/or the inner portion, the amount of force that the eye in which lens 100 is placed can exert on the lens 100 and the like factors. The amount or degree of near power correction obtainable from lens 100 can be controlled, or at least partially controlled, by varying one or more of these factors.

The embodiments of the optical element 105 described thus far, have a resting configuration when no forces being applied that are lower power or more flat. During accommodation when the ciliary body pushes against the force translation elements 110, the optical element 105 can take on a more spherical, higher power configuration. It should be appreciated, however, that the optical element 105 can also mimic more closely a natural lens. In this embodiment, the optical element 105 is high power or more spherical at a resting configuration when no forces are being applied to it. In this embodiment, the ciliary body relaxes during disaccommodation and applies tension to the force translation elements 110 which translate a force on the optical element 105 such that the optical element 105 flattens for low power and returns to the spherical configuration during accommodation with the ciliary body contracts. In such a configuration, the force translation element 110 could incorporate a more robust mechanism of attachment to the tissues.

The lenses described herein have the ability, in cooperation with the eye, to be reshaped to provide for both distance focus and near focus, and to be returned to its first configuration in which only distance focus is provided. The amount of force required to effect a shape change in the optical element 105 is generally less than that of moving the optical element 105 axially along the optical axis to achieve the desired change in diopter. The change in diopter achieved by a shape change is also generally larger than the change in diopter achieved by an axial displacement. The optical element 105 can have a power in the range of about ±1 D to about ±4 D or about ±5 D or about ±6 D. In an embodiment, the underlying power of the lens can be within the range of about ±5 D. In an embodiment, the underlying power of the lens can be within the range of about ±3 D. It should be appreciated that the optical element 105 can also have a larger power in the range of about ±20 D.

Figure 4:
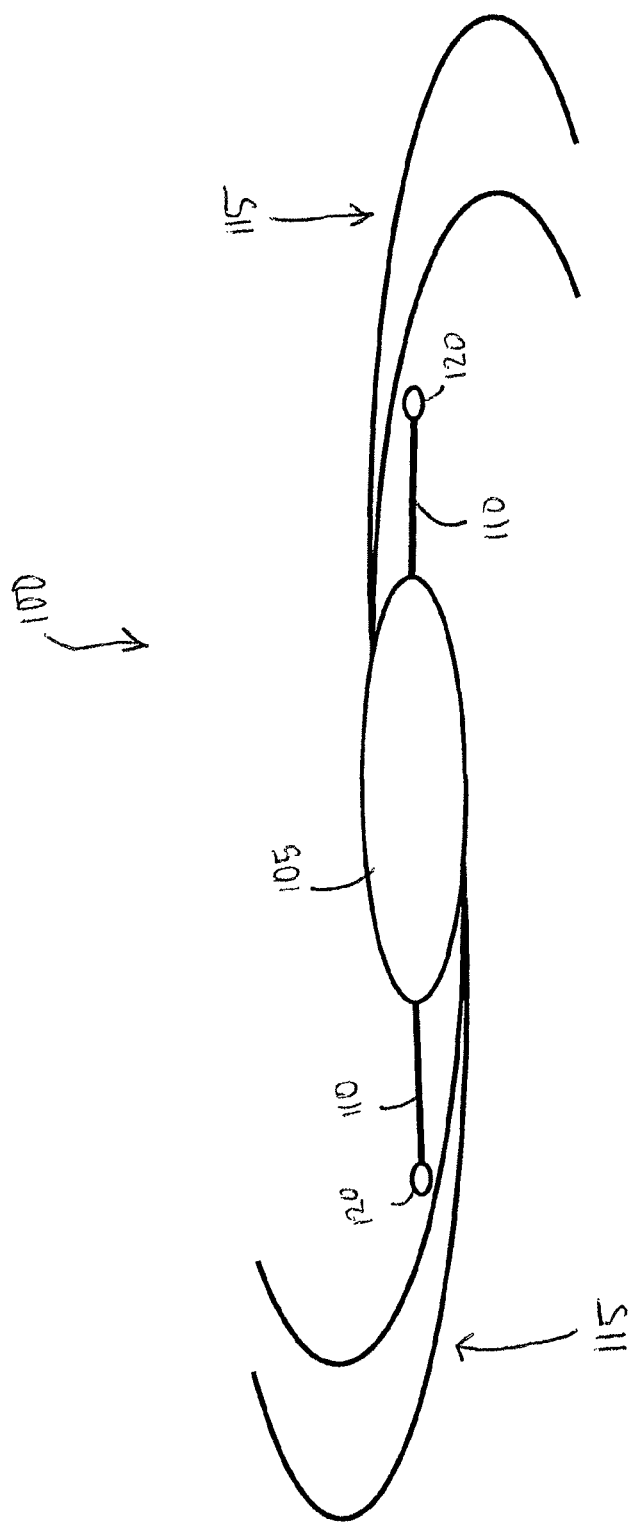
FIG. 4 depicts a schematic view of another embodiment of a lens having haptics and force translation elements.

The force translation elements 110 contact the eye tissue by way of an attachment portion 120 (see FIG. 4). The mode of attachment provided by the attachment portion 120 can vary. Generally, the attachment portion 120 avoids piercing or causing trauma to the ciliary body 25. The attachment portion 120 can interfere with the tissues such that movement of the ciliary body 25, ciliary processes 27 or zonules 30 can be transferred through the force translation elements 110 to the optical element 105 without causing trauma to the tissues themselves. The attachment portion 120 can be formed of a material that is generally softer or more elastic than the force translation elements 110. This provides a more forgiving surface against which the tissues can abut such that piercing of the tissues and inadvertent trauma are avoided. This also allows for the attachment portion 120 to provide a better fit in that there is some room for error in the overall length and size of the lens 100 and its components. The elasticity of the material can also for a one-size-fits-all approach such that even if the measurement was not exact, the length of the translation elements 110 and attachment portions 120 would be sufficient to effect shape change of the optical element 105 when needed while avoiding constant shape change or tissue damage.

Figure 6A:
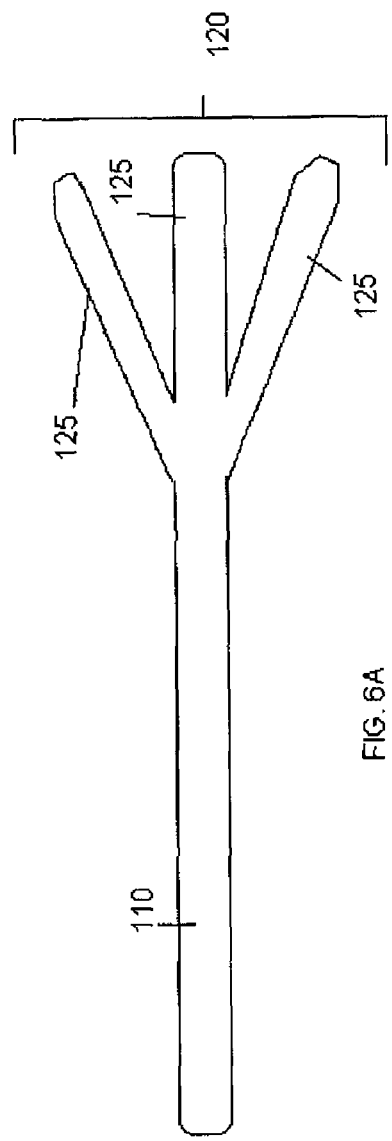
FIGS. 6A-6B depict schematic views of force translation elements.

As an example, the attachment portion 120 can be a generally rigid, elongate rod or plurality of rods 125 (see FIG. 6A) positioned between and interfering with one or more zonules 30 or ciliary processes 27. The rods 125 can be straight, curved, or have a bend at a particular angle relative to the longitudinal axis of the force translation element 110. As an example, the plurality of rods 125 can be curved such that they form a cup that can interdigitate between the ciliary processes 27 and/or zonules 30. The plurality of rods 125 can extend to the ciliary body 25 with or without making contact with the ciliary body 25.

Figure 6B:
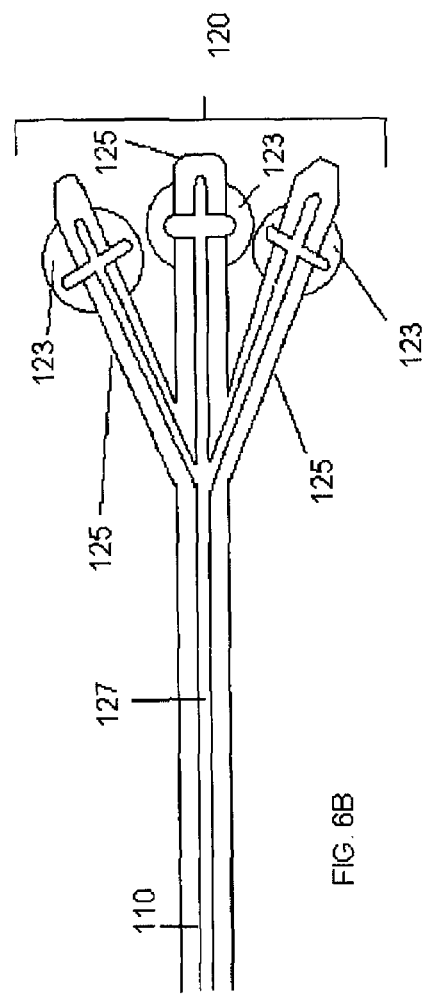

The attachment portion 120 can also have a three-dimensional shape that fills a space surrounding the zonules 30 or ciliary processes 27 or that fills the space above the ciliary body 25. As an example, the attachment portion 120 can have a wedge shape such that the force translation elements 110 extends between the ciliary processes 27 and the attachment portion 120 wedges up against the ciliary body 25. The attachment portion 120 can also include a three-dimensional expandable element 123 such as a bag, balloon or bulb coupled near an end of the force translation element 110. FIG. 6B illustrates an attachment portion 120 of an embodiment of a force translation element 110 having a plurality of rods 125. One or more of the plurality of rods 125 can include an expandable element 123 near a distal end region. A channel 127 can extend through an interior of the force translation element 110 into at least a portion of each of the plurality of rods 125 such that the channel 127 communicates with the expandable elements 123. A fluid (including a gas or liquid or gel) can be injected into a port or other structure positioned along the force translation element 110 and into the channel 127 such that the expandable element 123 expands outward into one or more directions. The position of the port can vary, but is generally located so that it does not interfere with the optical part of the device. In some embodiments, the expandable elements 123 can expand three-dimensionally such that they fill the space between the ciliary processes 27 or around the ciliary body 25 or on top of the ciliary processes 27 and covering the ciliary body 25. The expandable elements 123 can be filled with a material to provide the desired three-dimensional shape, such as silicone oil, hydrogel, saline or other material.

As shown in FIGS. 7A and 7B, the attachment portion 120 can include a coating 129 made of a material such as glue, hydrogel or other flowable material (see FIGS. 7A-7B). The coating 129 can fix the attachment portion 120 in place. The coating 129 can also act to fill a three-dimensional space surrounding a particular tissue site to help secure the lens 100. The coating 129 can be injected through a port and into a channel 127 extending through the interior of the force translation element 110 into the attachment portion 120. One or more openings 131 positioned near a distal end region of the attachment portion 120 can allow for the material to flow from the channel 127 to an external surface of the attachment portion 120 therein coating the external surface.

Soft tissue integration of the attachment portion 120 can be achieved by positioning the attachment portion 120 in direct contact with one or more of the ciliary tissues such that a minimal level of tissue irritation is achieved to set off a healing response. Upon tissue irritation, a minor inflammatory response ensues that is enough to cause the attachment portion 120 to become incorporated into the ciliary processes 27 or ciliary body 25 without interfering with the physiological role of the tissues. Tissue growth into and/or around the attachment portion 120 and integration of the device into the tissue can be achieved without piercing or causing trauma to the tissue, for example affecting its ability to produce aqueous humor.

It should also be appreciated that a combination of attachment portions 120 with or without soft tissue integration are considered herein. For example, one or more expandable elements 123 can be coupled to an end region of the attachment portion 120 that are also filled and coated with a material that provides fixing power such as glue or another flowable material. Further, the expanded shape of the expandable element 123 can provide certain characteristics to the attachment portion 120. For example, the expandable element 123 when filled can form a wedge shape such that it can be used as described above to wedge up against the ciliary body 25 or between the ciliary processes 27 when filled upon implantation. The expandable elements 123 can also provide a degree of customization to the attachment portion 120 such that the fit can be modified during implantation. The expandable element 123 can be positioned at a distal end region of the attachment portion 120 such that upon filling the expandable element 123 provides a customized size that provides the most beneficial fit to the device for a particular patient.

The force translation elements 110 and/or the attachment portion 120 of the lens can be customized for length, angle and position relative to various structures of the eye. For example, the angle at which the force translation elements 110 extend from the optical element 105 can play a role in the distance D away from the natural lens or previously implanted IOL that the lens 100 is implanted, which in turn can impact the focal power. Further, the length of the force translation elements 110 can affect whether or not the force translation elements 110 physically contact the ciliary body or neighboring tissues. If the force translation elements 110 are too long and make contact with the ciliary body in a resting state it is possible that the tissue structures can be damaged or the optical element 105 can remain in a constant state of accommodation. Alternatively, if the force translation elements 110 are too short it is possible that not enough shape change would be achieved upon ciliary muscle contraction to effect proper accommodation. It is desirable, therefore, to customize and adjust the length, angle, position or other characteristics of the force translation elements 110 and/or the attachment portion 120 upon implantation. It should be appreciated that the customization can take place prior to implantation if the appropriate measurements are known in advance of the procedure. Alternatively, customization can take place on-the-fly during implantation or after implantation of the lens 100.

The length of each force translation element 110 can be adjusted by a variety of mechanisms including sliding, twisting, turning, cutting, rolling, expanding, etc. For example, the force translation element 110 can be unrolled upon implantation in an outward direction from the optical element 105 until the optimum length is achieved for proper accommodation to occur upon ciliary muscle contraction. Alternatively, the force translation element 110 can be twisted to reduce the overall length it extends outward from the optical element 105. The force translation element 110 can also be manually cut to an appropriate length.

The force translation element 110 and/or the attachment mechanism 120 can be formed of a shape-memory material or other stimuli-responsive material that has the capability of changing shape under an external stimulus. For example, the stimulus can be a temperature change or exertion of an external force (compression or stretching). The shape-memory material can be activated to extend to a pre-set length, shape or angle upon application of energy such as heat. The force translation element 110 and/or the attachment mechanism 120 can be formed of an elastic or super-elastic material such as Nitinol.

The force translation element 110 and/or the attachment mechanism 120 can be formed of or coated with a material that expands upon implantation in the eye. The material can expand along a longitudinal axis of the structure or the material can expand in three-dimensionally so as to fill a void adjacent the component. For example, the expanded material can fill a void adjacent the force translation element 110 and/or attachment mechanism 120 such as the region between the ciliary processes. Expandable materials can include, but is not limited to for example, hydrogel, foam, lyophilized collagen, swelling acrylic, or any material that gels, swells, or otherwise expands upon contact with body fluids. The expandable material can be positioned such that it causes the force translation element 110 to move from a retracted state to an expanded state such that it extends between or against an anatomical structure. The expandable material can also coat the attachment mechanisms 120 and aid in the attachment mechanism 120 taking on a preferred shape. For example, the attachment mechanism 120 can be a plurality of rods coated by the expandable material such that upon implantation the rods are forced outward away from one another.

As mentioned above, the force translation element 110 can be coupled to a region of the haptic 115. In an embodiment, the haptic 115 can be positioned within the sulcus and the force translation element 110 can be angled downward to reach the ciliary body. The force translation element 110 can be twisted around the haptic 115 to achieve a desired length. Alternatively, the force translation element 110 can be coupled to the haptic 115 in such a way that it can be manually moved along the length of the haptic 115 until the desired extension towards the ciliary body is achieved.

The material of the components of the lenses described herein can vary. As mentioned above, the force translation elements 110 and haptics 115, if present, are generally formed of a material having a harder durometer than the optical element 105 or the attachment mechanism 120 such that they can translate forces applied by the surrounding tissues to effect shape change and/or change in spatial configuration of the optical element 105. The force translation elements 110, attachment mechanism 120, haptics 115 (if present) and optical element 105 can each be the same material, but may have a hardness that differs to achieve the desired functional characteristics when implanted.

Suitable materials for the preparation of the optical element 105 disclosed herein vary and include materials that are known in the art. As an example, materials can include, but are not limited to, acrylic polymers, silicone elastomers, hydrogels, composite materials, and combinations thereof. Materials considered herein for forming various components are described in U.S. Patent Publication Nos. 2009/0234449 and 2009/0292355, which are each incorporated by reference herein in their entirety. The optical element 105 can also be formed from a photosensitive silicone to facilitate post-implantation power adjustment as taught in U.S. Pat. No. 6,450,642, entitled LENSES CAPABLE OF POST-FABRICATION POWER MODIFICATION, the entire contents of which are hereby incorporated by reference herein.

Suitable materials for the production of the subject force translation elements 110 include but are not limited to foldable or compressible materials or hard materials, such as silicone polymers, hydrocarbon and fluorocarbon polymers, hydrogels, soft acrylic polymers, polyesters, polyamides, polyimides, polyurethane, silicone polymers with hydrophilic monomer units, fluorine-containing polysiloxane elastomers and combinations thereof.

A high refractive index is a desirable feature in the production of lenses to impart high optical power with a minimum of optic thickness. By using a material with a high refractive index, visual acuity deficiencies may be corrected using a thinner IOL.

The optical element 105 can also be formed from layers of differing materials. The layers may be arranged in a simple sandwich fashion, or concentrically. In addition, the layers may include a series of polymer layers, a mix of polymer and metallic layers, or a mix of polymer and monomer layers. In particular, a Nitinol ribbon core with a surrounding silicone jacket may be used for any portion of the lens 100 except for the optics; an acrylic-over-silicone laminate may be employed for the optics. A layered construction may be obtained by pressing/bonding two or more layers together, or deposition or coating processes may be employed.

Where desired, various coatings are suitable for one or more components of the lens 100. A heparin coating may be applied to appropriate locations to prevent inflammatory cell attachment (ICA) and/or posterior capsule opacification (PCO); possible locations for such a coating include the optical element 105. Coatings can also be applied to the lens 100 to improve biocompatibility; such coatings include "active" coatings like P-15 peptides or RGD peptides, and "passive" coatings such as rapamycin, steroids, heparin, and other mucopolysaccharides, collagen, fibronectin and laminin. Other coatings, including hirudin, Teflon, Teflon-like coatings, PVDF, fluorinated polymers, and other coatings which are inert may be employed to increase lubricity at locations on the lens system, or Hema or silicone can be used to impart hydrophilic or hydrophobic properties to portions of the lens 100.

One or more of the lens components can also be coated with a therapeutic or other agent that ameliorates a symptom of a disease or disorder including, for example, steroids, small molecule drugs, proteins, nucleic acids, polysaccharides, and biologics or combination thereof. Therapeutic agent, therapeutic compound, therapeutic regimen, or chemotherapeutic include conventional drugs and drug therapies, including vaccines, which are known to those skilled in the art. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, proteins, peptides or peptidomimetics, bioactive agents, photosensitizing agents, radionuclides, toxins, anti-metabolites, signaling modulators, anti-cancer antibiotics, anti-cancer antibodies, angiogenesis inhibitors, radiation therapy, chemotherapeutic compounds or a combination thereof. The drug may be any agent capable of providing a therapeutic benefit. In an embodiment, the drug is a known drug, or drug combination, effective for treating diseases and disorders of the eye. In non-limiting, exemplary embodiments, the drug is an anti-infective agent (e.g., an antibiotic or antifungal agent), an anesthetic agent, an anti-VEGF agent, an anti-inflammatory agent, a biological agent (such as RNA), an intraocular pressure reducing agent (i.e., a glaucoma drug), or a combination thereof. Non-limiting examples of drugs are provided below.

In an embodiment, the lens 100 and/or the mold surfaces are subjected to a surface passivation process to improve biocompatibility. This may be done via conventional techniques such as chemical etching or plasma treatment.

Once formed, the subject force translation elements 110 can be permanently attached to optical element 105 by numerous methods including but not limited to fastening within a pre-formed optic slot using glue, staking, plasma treatment, friction, or like means or combinations thereof.

Furthermore, appropriate surfaces (such as the outer edges/surfaces of the contacting elements, accommodating elements, etc.) of the lens components can be textured or roughened to improve adhesion to the adjacent tissue surfaces. This can be accomplished by using conventional procedures such as plasma treatment, etching, dipping, vapor deposition, mold surface modification, etc.

In an embodiment, the selected material and lens configuration is able to withstand secondary operations after molding/casting such as polishing, cleaning and sterilization processes involving the use of an autoclave, or ethylene oxide or radiation. After the mold is opened, the lens can undergo deflashing, polishing and cleaning operations, which typically involve a chemical or mechanical process, or a combination thereof. Some suitable mechanical processes can include tumbling, shaking and vibration; a tumbling process may involve the use of a barrel with varying grades of glass beads, fluids such as alcohol or water and polishing compounds such as aluminum oxides. Process rates are material dependent; for example, a tumbling process for silicone can utilize a 6" diameter barrel moving at 30-100 RPM. It is contemplated that several different steps of polishing and cleaning may be employed before the final surface quality is achieved.

A curing process may also be desirable in manufacturing the components of the lens 100. If the lens is produced from silicone entirely at room temperature, the curing time can be as long as several days. If the mold is maintained at about 50° C., the curing time can be reduced to about 24 hours. If the mold is preheated to 100-200° C., the curing time can be as short as about 3-15 minutes. The time-temperature combinations vary for other materials.

It should be appreciated that the lenses described herein can be implanted in a phakic or pseudophakic patient. In an exemplary implantation procedure, an IOL implantation is performed anterior to the natural crystalline lens or anterior to a previously-implanted IOL. Although the implantation procedure can vary, one procedure can be performed as follows. One or more clear corneal incisions can be formed. A first incision can be formed for IOL insertion and a second incision can be formed for manipulation and assistance of positioning the IOL. A viscoelastic substance can be inserted into the eye, such as to at least partially fill the anterior chamber and/or an area between the iris and the intra-capsular IOL. The IOL can be inserted into position in the eye and the force-translation elements inserted into a desired position and connected to the ciliary body. One or more IOL can be inserted into the ciliary sulcus and the viscoelastic substance washed out of the eye. A check may then be performed to verify that the corneal incisions are appropriately sealed. Any of a variety of instruments may be used in conjunction with the procedure. Moreover, it should be appreciated that the aforementioned steps may be performed in a different order than described above.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An intraocular lens, comprising:
a compressible, shape-changing lens body, an optical axis passing through the lens body when implanted in an eye, wherein the lens body comprises a core lens portion and an outer lens portion comprising an anterior portion having an anterior surface, wherein the anterior portion of the outer lens portion has a center section having a reduced thickness relative to a perimeter section surrounding the center section, wherein the center section is configured to bow along the optical axis of the lens body relative to the perimeter section upon application of a compressive force directed radially inward on the lens body and upon an increase in internal pressure of the core lens portion thereby creating a shape change for near-vision correction power while the perimeter section is resistant to reshaping under the compressive force and maintains distance-vision correction power away;
at least two haptics, each of the at least two haptics having a first end attached directly to and extending outward from the lens body to form a first coupling, each of the at least two haptics additionally having a second end region opposite the first end configured to contact a region of the eye to anchor and center the lens body within a portion of the eye; and
an accommodating element coupled to the lens body and comprising a rigid, force translation element having a first end coupled directly to the lens body forming a second coupling and a second end opposite the first end, the force translation element configured to extend away from the optical axis and outside of a capsular bag at a different angle with respect to the optical axis than an angle of each of the at least two haptics and towards a ciliary structure, wherein the second end of the force translation element is coupled to an attachment portion extending at an angle relative to the second end and relative to a longitudinal axis of the force translation element, wherein the rigid, force translation element is configured to transmit movement of the ciliary structure during ciliary muscle contraction into the compressive force directed radially inward on the compressible lens body to effect the shape change.

2. The intraocular lens of claim 1, wherein the force translation element incorporates a mechanism for customizing a length of the force translation element.

3. The intraocular lens of claim 2, wherein the mechanism can be used during or after implantation of the intraocular lens into the eye.

4. The intraocular lens of claim 2, wherein the mechanism for customizing the length of the force translation element is selected from the group consisting of sliding, twisting, turning, cutting, rolling, expanding, bending, and applying energy to the force translation element.

5. The intraocular lens of claim 1, wherein the at least two haptics are separate from the accommodating element.

6. The lens of claim 1, wherein at least one of the lens body and the force translation element is coated with an agent having biological activity.

7. The lens of claim 6, wherein the agent is selected from the group consisting of P-15 peptide, RGD peptide, rapamycin, steroid, heparin, mucopolysaccharide, collagen, fibronectin, laminin, small molecule drug, protein, peptide, nucleic acid, polysaccharide, vaccine, cell growth inhibitor, cell death promoter, cytokine, growth factor, a peptidomimetic agent, photosensitizing agent, radionuclide, toxin, an anti-metabolite, signaling modulator, anti-cancer antibiotic, anti-cancer antibody, angiogenesis inhibitor, radiation therapy, chemotherapeutic compound, antiinfective agent, antibiotic agent, antifungal agent, anesthetic agent, anti-VEGF agent, anti-inflammatory agent, a biological agent, RNA, an intraocular pressure reducing agent, and a glaucoma drug.

8. The lens of claim 1, wherein the first end region of the force translation element is coupled to an equator region of the lens body.

9. The lens of claim 1, further comprising a plurality of force translation elements coupled near an equator region of the lens body.

10. The lens of claim 1, wherein the ciliary structure is selected from the group consisting of the ciliary muscle, the ciliary body, a ciliary process, and a zonule.

11. The lens of claim 10, wherein the attachment portion coupled to the second end region of the force translation element is configured to contact the ciliary structure upon contraction movements of the ciliary muscle.

12. The lens of claim 11, wherein the attachment portion has a wedge shape so as not to penetrate the ciliary structure upon contact with the ciliary structure.

13. The lens of claim 11, wherein the attachment portion is formed of an elastic material.

14. The lens of claim 11, wherein the attachment portion comprises one or more rods.

15. The lens of claim 14, wherein the one or more rods are curved to form a cup that is configured to interdigitate between one or more of the ciliary structures.

16. The lens of claim 11, wherein the attachment portion comprises a three dimensional element that expands outward into one or more directions such that it fills a space adjacent the ciliary structure.

17. The lens of claim 1, further comprising a second intraocular lens configured to be positioned posteriorly to the lens body and within the capsular bag of the eye.

18. The lens of claim 1, wherein the lens body is configured to be positioned anteriorly to a natural lens of the eye.

19. The lens of claim 1, wherein the lens body is configured to be positioned within the capsular bag of the eye.

20. The lens of claim 1, wherein the at least two haptics are configured to be positioned within a ciliary sulcus between a posterior surface of the iris and an anterior surface of the ciliary body.

21. A method of implanting the intraocular lens of claim 1, the method comprising:
    forming an incision in a cornea of an eye;
    inserting the intraocular lens into the eye through the incision;
    positioning the ocular element of the intraocular lens either inside or outside the capsular bag; and
    extending the accommodating element towards the ciliary structure such that during relaxation of the ciliary muscle the second end region of the force translation element is adjacent, but does not abut the one or more ciliary structures and wherein during inward ciliary muscle contraction the second end region of the force translation element abuts the one or more ciliary structures.

22. The method of claim 21, wherein the at least two haptics are positioned into a ciliary sulcus between a posterior surface of the iris and an anterior surface of the ciliary body.

23. The method of claim 21, wherein the at least two haptics are placed in the capsular bag.

24. The method of claim 21, wherein the force translation element is coupled to an equator region of the lens body and transfers the force to the equator region of the lens body in a direction toward the optical axis.

25. The method of claim 24, wherein contraction of the ciliary muscle and inward movement of the ciliary body additionally changes spatial configuration of the lens body axially along the optical axis in an anterior direction.

* * * * *

UNITED STATES PATENT AND TRADEMARK OFFICE
CERTIFICATE OF CORRECTION

PATENT NO. : 9,913,712 B2
APPLICATION NO. : 14/067839
DATED : March 13, 2018
INVENTOR(S) : Cary Reich, Eugene de Juan and Yair Alster Page 1 of 1

It is certified that error appears in the above-identified patent and that said Letters Patent is hereby corrected as shown below:

In the Claims

Please delete "away" in Column 14, Line 53 of Claim 1.

Signed and Sealed this
Nineteenth Day of May, 2020

Andrei Iancu
*Director of the United States Patent and Trademark Office*